(12) United States Patent
Kolbe et al.

(10) Patent No.: US 8,920,785 B2
(45) Date of Patent: Dec. 30, 2014

(54) COSMETIC OR DERMATOLOGICAL PREPARATIONS WITH A CONTENT OF ONE OR MORE THIAZOLE DERIVATES

(75) Inventors: Ludger Kolbe, Dohren (DE); Cathrin Scherner, Norderstedt (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 13/634,586

(22) PCT Filed: Feb. 21, 2011

(86) PCT No.: PCT/EP2011/052479
§ 371 (c)(1),
(2), (4) Date: Nov. 1, 2012

(87) PCT Pub. No.: WO2011/117034
PCT Pub. Date: Sep. 29, 2011

(65) Prior Publication Data
US 2013/0039870 A1 Feb. 14, 2013

(30) Foreign Application Priority Data
Mar. 23, 2010 (DE) .......................... 10 2010 012 594

(51) Int. Cl.
*A61K 8/49* (2006.01)
*A61Q 19/02* (2006.01)
*C07D 471/04* (2006.01)
*C07D 417/12* (2006.01)
*C07D 277/42* (2006.01)
*C07D 277/48* (2006.01)

(52) U.S. Cl.
CPC . *A61K 8/49* (2013.01); *A61Q 19/02* (2013.01); *C07D 417/12* (2013.01); *C07D 277/48* (2013.01)
USPC ............. 424/62; 544/331; 544/133; 548/193; 548/156; 548/195; 546/270.7; 546/119

(58) Field of Classification Search
None
See application file for complete search history.

(56) References Cited

U.S. PATENT DOCUMENTS

| 2003/0158199 A1 | 8/2003 | Stieber et al. |
| 2004/0110810 A1 | 6/2004 | Ciufolini et al. |
| 2005/0239852 A1 | 10/2005 | Ciufolini et al. |
| 2007/0042997 A1 | 2/2007 | Itai et al. |
| 2008/0255141 A1 | 10/2008 | Ciufolini et al. |
| 2010/0324096 A1* | 12/2010 | Hanyu et al. .................. 514/342 |
| 2012/0053186 A1 | 3/2012 | Ciufolini et al. |
| 2012/0134944 A1 | 5/2012 | Hanyu et al. |

FOREIGN PATENT DOCUMENTS

| EP | 1437348 A1 | 7/2004 |
| EP | 1649 852 * | 4/2006 ............. A61P 17/00 |
| EP | 1649852 A1 | 4/2006 |
| WO | 2004014903 A1 | 2/2004 |
| WO | 2008101693 A2 | 8/2008 |
| WO | 2009099195 A1 | 8/2009 |
| WO | WO2009099195 * | 8/2009 |

OTHER PUBLICATIONS

Germanas et al. "Discovery of small-molecule inhibitors of tyrosine" Bioorganic & Medicinal Chemistry Leters, Pergamon, Elsevier Science, GB, vol. 17, No. 24, Oct. 12, 2007 pp. 6871-6875.*
2-Amino-4-arylthiazoles and their thiazolylamides as antifungal agents. 1 Journal of the Institution of Chemists (India) (1997), 69, (4), 113-115. Publisher: (Institution of Chemists (India).*
M. Seiberg et al., 2000, J. Cell. Sci., 113: 3093-101.
A. Kligman, 1975, Arch. Dermatol., 111: 40-48.
Winder, A. J. and Harris H., New assays for the tyrosine hydroxylase and dopa oxidase activities of tyrosinase. Eur. J. Biochem. (1991), 198, 317-26.
Germanas et al: "Discovery of small-molecule inhibitors of tyrosinase", Bioorganic & Medicinal Chemistry Letters, Pergamon, Elsevier Science, GB, vol. 17, No. 24, Oct. 12, 2007, pp. 6871-6875.
Lynch D E et al: "The hydrogen-bonding networks of 2-amino-4-phenyl-1,3-thiazole derivatives", Crystal Engineering, Elsevier Science Publishers, Barking, GB, vol. 5, No. 2, Jun. 1, 2002, pp. 123-136.

* cited by examiner

*Primary Examiner* — Robert A Wax
*Assistant Examiner* — Danah Al-Awadi
(74) *Attorney, Agent, or Firm* — Abel Law Group, LLP

(57) ABSTRACT

Cosmetic or dermatological preparations having an effective content of one or more thiazoles of the general formula.

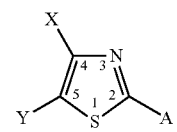

20 Claims, No Drawings

COSMETIC OR DERMATOLOGICAL PREPARATIONS WITH A CONTENT OF ONE OR MORE THIAZOLE DERIVATES

BACKGROUND OF THE INVENTION

1. Field of the Invention

The present invention relates to cosmetic cosmetic or dermatological preparations having a content of one or more thiazoles against unwanted pigmentation of the skin.

2. Discussion of Background Information

Melanocytes are responsible for pigmentation of the skin and may be found in the lowest layer of the epidermis, the Stratum basale, in addition to the basal cells as pigment-forming cells—occurring according to skin type either singly or more or less aggregated.

Melanocytes contain as characteristic cell organelle melanosomes, in which the melanin is formed. Melanin is formed to an increased extent, inter alia, on excitation by UV radiation. The melanin is transported via the living layers of the epidermis (keratinocytes) ultimately into the Horny layer (corneocytes) and gives rise to a more of less expressed brownish to brown-black skin color.

Melanin is formed as the last step of an oxidative process in which tyrosine, with the participation of the enzyme tyrosinase, is converted via a plurality of intermediates to the brown to brown-black eumelanins (DHICA and DHI melanin), or with the participation of sulfur compounds to form the reddish pheomelanin. DHICA and DHI melanin are formed via the shared intermediates dopaquinone and dopachrome. The latter is converted, in part with the participation of further enzymes either into indole-5,6-quinonecarboxylic acid or indole-5,6-quinone, from which the two aforementioned eumelanins are formed.

The formation of pheomelanin proceeds, inter alia, via the intermediates dopaquinone and cysteinyldopa. The expression of the melanin-synthesizing enzymes is controlled by a specific transcription factor (microphthalmia-associated transcription factor, MITF). In addition to the described enzymatic processes of melanin synthesis, in the melanosomes, still further proteins are important for melanogenesis. An important role appears to be assigned here to what is termed p-protein, the exact function is still unclear.

Apart from the above described process of melanin synthesis in the melanocytes, in the pigmentation of the skin, the transfer of the melanosomes, the remaining thereof in the epidermis and also the breakdown thereof and breakdown of the melanin are also of critical importance. It has been found that for the transport of melanosomes from the melanocytes into the keratinocytes, the PAR-2 receptor is of importance (M. Seiberg et al., 2000, J. Cell. Sci., 113: 3093-101).

In addition, size and shape of the melanosomes have an effect on their light-scattering properties and therefore the skin color appearance. Thus, in black Africans, large spheroidal melanosomes singly are found to a greater extent, whereas in Caucasians, somewhat smaller melanosomes occurring in groups are found.

Problems with hyperpigmentation of the skin have varied causes, or are associated symptoms of many biological processes, e.g. UV radiation (e.g. freckles, Ephelides), genetic disposition, disturbed pigmentation of the skin on wound healing or scar formation (post-inflammatory hyperpigmentation) or on skin ageing (e.g. Lentigines seniles).

After inflammatory reactions, the pigmentation system of the skin reacts with sometimes opposing reactions. Both post-inflammatory hyperpigmentations and also hypopigmentations can occur. Post-inflammatory hypomelanoses frequently occur, inter alia, in combination with atopy, Lupus erythematosus and psoriasis. The under-standing of the varying forms of reaction of the pigmentation system of human skin as a consequence of inflammatory symptoms is very incomplete.

Problems with post-inflammatory hyperpigmentation frequently occur with darker skin types. Especially in dark-skinned males, the problem of *Pseudofollikulitis barbae* is known, which is accompanied with cosmetically undesirable pigmentation disorders or is followed thereby. Also forms of melasma which occur especially in the face and décolleté regions of women of Asiatic origin, and also various types of irregular pigmentation of the skin are included in the post-inflammatory hyperpigmentations. In addition, dark eye rings are also considered to be a type of post-inflammatory hyperpigmentation, wherein the underlying inflammation usually proceeds subclinically.

In many cases, such post-inflammatory pigmentation disorders are further increased by the action of sunlight (UV light), without a UV-induced inflammation (sunburn) occurring.

Active ingredients and preparations are known which counteract skin pigmentation. Those in practical use are substantially formulations based on hydroquinone, some of which, however, only display their activity after application for several weeks, the excessively long application of which, on the other hand, is of concern for toxicological reasons. Albert Kligman et al. developed what is termed a "triformula" which is a combination of 0.1% Tretinoin, 5.0% hydroquinone, 0.1% dexamethasone (A. Kligman, 1975, Arch. Dermatol., 111: 40-48). However, this formulation is also highly controversial because of possible irreversible changes in the pigmentation system of the skin.

In addition, skin-peeling methods (chemical and mechanical peelings) are used, but which frequently are followed by inflammatory reactions, and owing to post-inflammatory hyperpigmentations occurring thereafter can even lead to greater rather than reduced pigmentation. All of these familiar methods which are also used for treating post-inflammatory hyperpigmentations, are distinguished by substantial side effects.

Therefore, it was the aim of the following invention to provide a remedy for the disadvantageous prior art.

SUMMARY OF THE INVENTION

The present invention provides a cosmetic or dermatological preparation that comprises one or more thiazoles of formula:

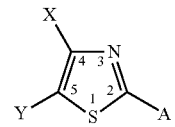

in which
A=—N($R_1$)$_2$, —S—$R_1$, —C—($R_1$)$_3$, —O—$R_1$, —CO—$R_1$, -morpholino, -morpholino derivatives;
$R_1$, X and Y can be different, in part identical or completely identical and, independently of one another represent:
$R_1$=—H, —$C_1$-$C_{24}$-alkyl (linear and branched), —$C_1$-$C_{24}$-alkenyl (linear and branched), —$C_1$-$C_{24}$-hydroxyalkyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -2-hydroxyphenyl, -3-hydroxyphenyl, -4-hydroxyphenyl, -pyridin-2-yl, -pyridin-3-yl, -pyridin-4-yl, pyridin-1(2H)-yl, -pyrimidin-2-yl, -pyrazin-2-yl, -pyrimidin-4-yl, -pyridazin-3-yl, -pyridazin-4-yl, -pyrimidin-2-yl, -pyrimidin-5-yl, -1,2,4-triazin-3-yl, -1,3,5-triazin-2-yl, -1,2,3-triazin-4-yl, -1,2,3-triazin-5-yl, -1,2,3,4-tetrazin-5-yl, -1,2,3,5-tetrazin-4-yl, -1,2,4,5-tetrazin-3-yl, -pentazin-6-yl, -morpholino, -thiazole, —C═O— alkyl (linear and branched), —C═O-alkenyl (linear and branched), —C═O—$C_1$-$C_8$-cycloalkyl, —C═O-aryl, —C═O-heteroaryl, —C═O-alkylaryl (linear and branched), —C═O-alkylheteroaryl (linear and branched), —C═O—NH-alkyl (linear and branched), —C═O—NH-alkenyl (linear and branched), —C═O—NH-cycloalkyl, —C═O—NH-aryl, —C═O—NH-heteroaryl, —C═O—NH-alkylaryl (linear and branched), —C═O—NH-alkylheteroaryl (linear and branched); X═—H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -2-phenyl, -3-phenyl, -4-phenyl, -2,4-dihydroxyphenyl, -2,3-dihydroxyphenyl, -2,4-dimethoxyphenyl, -2,3-dimethoxyphenyl; Y═H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl; and in which X and Y together may form an aromatic or aliphatic homo- or heterocyclic ring system having up to n ring-forming atoms, wherein n can have values from 5 to 8, and the respective ring system in turn may be substituted by up to n–1 substituents selected from one or more of alkyl groups, hydroxyl groups, carboxyl groups, amino groups, nitrile groups, sulfur-containing substituents, ester groups, and ether groups; the one or more thiazoles being present as free base or as cosmetically and dermatologically acceptable salt thereof.

In one aspect of the preparation, the one or more thiazoles may comprise at least one compound of formula:

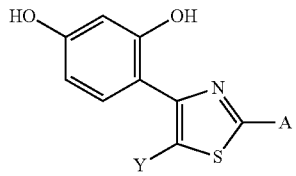

wherein A and Y are as defined above. For example, the one or more thiazoles may comprise at least one compound which is selected from compounds 1 to 28 set forth below, e.g., one or more compounds selected from compounds 1 to 7 and 20 to 28.

In another aspect, at least one of the one or more thiazoles may be present as a halide, a carbonate, an ascorbate, an acetate, or a phosphate.

In yet another aspect of the preparation, the one or more thiazoles may be present in a total concentration of from 0.00001% to 10% by weight, e.g., from 0.001% to 3.0% by weight, or from 0.005% to 1.0% by weight.

The present invention also provides a method of treating or preventing undesirable skin pigmentation. The method comprises applying to skin of a patient in need thereof a composition which comprises one or more thiazoles of the formula set forth above, including the various aspects thereof.

DETAILED DESCRIPTION OF THE INVENTION

The object of the invention is achieved by a cosmetic or dermatological preparation having an effective content of one or more thiazoles of the general formula

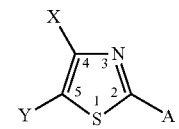

in which

A═—N($R_1$)$_2$*, —S—$R_1$, —C—($R_1$)$_3$*, —O—$R_1$, —CO—$R_1$, -morpholino, -morpholino derivatives; R1, X and Y can be different, in part identical or completely identical and, independently of one another can be:

$R_1$═—H, —$C_1$-$C_{24}$-alkyl (linear and branched), —$C_1$-$C_{24}$-alkenyl (linear and branched), —$C_1$-$C_{24}$-hydroxyalkyl (linear and branched), —$C_1$-$C_8$-cyclo alkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -2-hydroxyphenyl, -3-hydroxyphenyl, -4-hydroxyphenyl, -pyridin-2-yl, -pyridin-3-yl, -pyridin-4-yl, pyridin-1(2H)-yl, -pyrimidin-2-yl, -pyrazin-2-yl, -pyrimidin-4-yl, -pyridazin-3-yl, -pyridazin-4-yl, -pyrimidin-2-yl, -pyrimidin-5-yl, -1,2,4-triazin-3-yl, -1,3,5-triazin-2-yl, -1,2,3-triazin-4-yl, -1,2,3-triazin-5-yl, -1,2,3,4-tetrazin-5-yl, -1,2,3,5-tetrazin-4-yl, -1,2,4,5-tetrazin-3-yl, -pentazin-6-yl, -morpholino, -thiazole, —C═O-alkyl (linear and branched), —C═O-alkenyl (linear and branched), —C═O—$C_1$-$C_8$-cycloalkyl, —C═O-aryl, —C═O-heteroaryl, —C═O-alkylaryl (linear and branched), —C═O-alkylheteroaryl (linear and branched), —C═O—NH-alkyl (linear and branched), —C═O—NH-alkenyl (linear and branched), —C═O—NH-cycloalkyl, —C═O—NH-aryl, —C═O—NH-heteroaryl, —C═O—NH-alkylaryl (linear and branched), —C═O—NH-alkylheteroaryl (linear and branched);

X═—H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl;

Y═H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl;

X, Y═condensed aromatic;

wherein X and Y together can form aromatic or aliphatic homo- or heterocyclic ring systems having up to n ring-forming atoms, and wherein the number n can have values from 5 to 8, and the respective ring systems in turn can be substituted by up to n–1 alkyl groups, hydroxyl groups, carboxyl groups, amino groups, nitrile functions, sulfur-containing substituents, ester groups and/or ether groups.

Said thiazoles can be present either as free base or as salts: e.g. as fluoride, chloride, bromide, iodide, sulfate, carbonate, ascorbate, acetate or phosphate. In particular as halogen salts, such as, e.g. chloride and bromide.

Equally, the use of aforesaid thiazoles for treatment and/or prophylaxis of unwanted skin pigmentation is according to the invention.

Advantageously, X is selected from the group of phenyl groups substituted by one or more hydroxyl groups, wherein the following generic structure is preferred in which $R^2$ and $R^3$ can have the above defined properties.

In particular, the following species are advantageous:

Comp. 1

CAS No. 690695-60-4

Comp. 2

CAS No. 924173-79-5

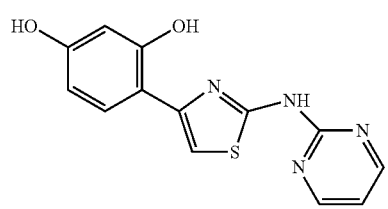

Comp. 3

CAS No. 690693-42-6

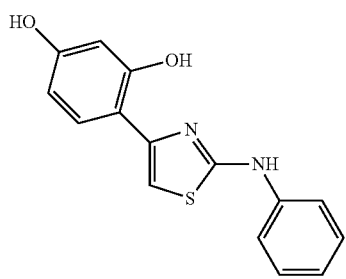

Comp. 4

CAS No. 1186650-75-8

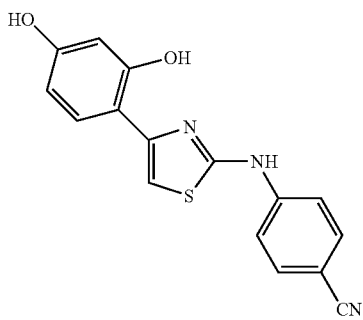

Comp. 5

CAS. No. 351520-00-08

Comp. 6

CAS. No. 875460-43-8

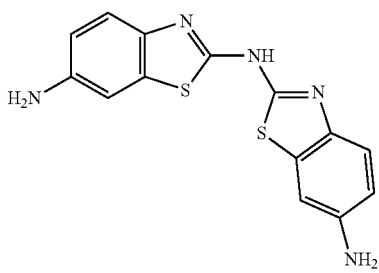

Comp. 7

CAS. No. 924455-10-7

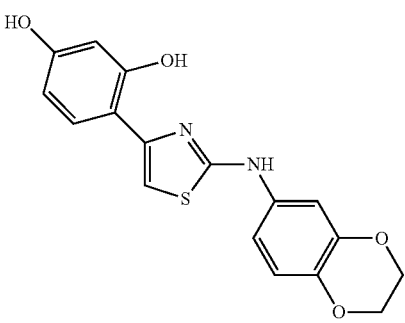

Comp. 8

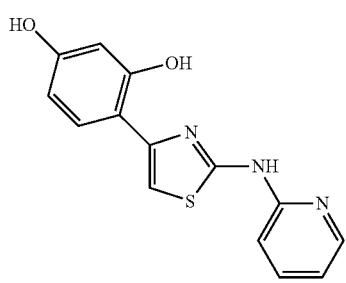

-continued

Comp. 9

CAS No. 695171-29-0

Comp. 10

CAS No. 488716-66-1

Comp. 11

Comp. 12

CAS No. 90850-44-5

Comp. 13

CAS No. 381186-92-1

Comp. 14

CAS No. 915873-63-1

Comp. 15

Comp. 16

Comp. 17

Comp. 18

Comp. 19

CAS No. 315703-17-4

-continued

Comp. 20

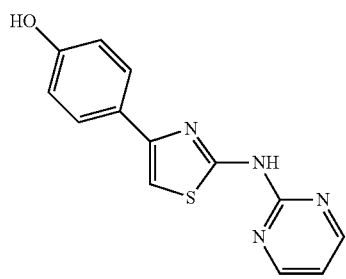

CAS No. 708289-74-1

Comp. 21

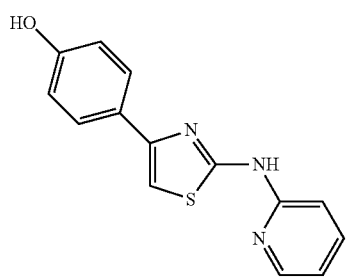

CAS No. 708991-99-5

Comp. 22

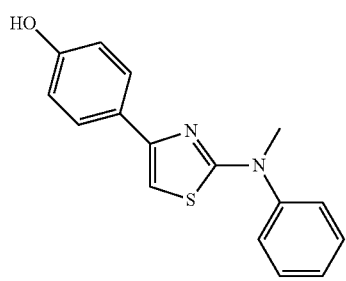

Comp. 23

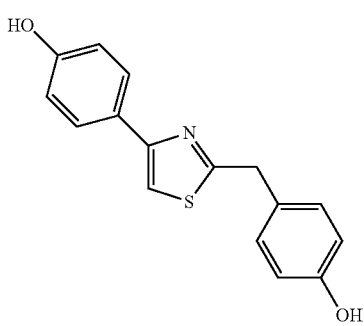

Comp. 24

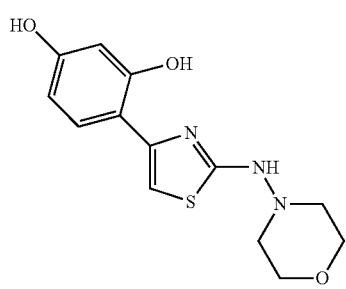

-continued

Comp. 25

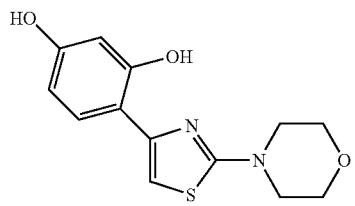

CAS No. 923850-84-4

Comp. 26

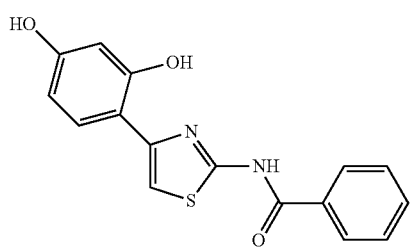

Comp. 27

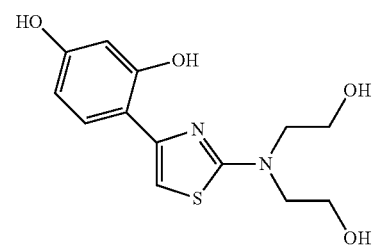

Comp. 28

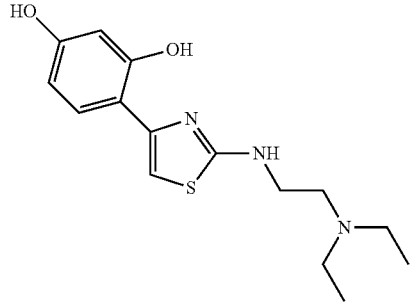

Compounds Comp. 1 to Comp. 7 and Comp. 20 to Comp. 28 are those preferred according to the invention.

The synthesis of thiazoles is described very well in the chemical literature, and synthesizing the substances is therefore possible without problems for chemists trained in the art. Many of the substances described by us are clearly characterized by a CAS No. and can be obtained from various manufacturers of fine chemicals.

The efficacy of the thiazoles has been verified using an enzyme test by measuring the conversion of L-DOPA to L-dopaquinone by a human tyrosinase. In this method that is known from the literature (Winder, A. J. and Harris H., New assays for the tyrosine hydroxylase and dopa oxidase activities of tyrosinase. Eur. J. Biochem. (1991), 198, 317-26), the reaction product L-dopaquinone is reacted with MBTH (3-methyl-2-benzothiazoline hydrazone) is converted to form a pink-colored substance, the increase of which over time is measured by absorption at 490 nm. In table one, efficacy data for some of the claimed substances are shown by way of example. It may be concluded therefrom that the substances according to the invention are extremely effective pigmentation-inhibiting substances.

TABLE 1

Inhibition of tyrosinase activity by thiazoles

| Substance | Inhibition (% of control) | Concentration |
| --- | --- | --- |
| Compound 1 | 93.1 | 100 μg/ml |
| Compound 2 | 100% | 100 μg/ml |
| Compound 6 | 87.4% | 100 μg/ml |
| Compound 20 | 61.3% | 100 μg/ml |
| Compound 21 | 87.6% | 100 μg/ml |
| Compound 22 | 87.9% | 100 μg/ml |
| Compound 24 | 82.9% | 100 μg/ml |
| Compound 25 | 90.3% | 100 μg/ml |
| Compound 26 | 100% | 100 μg/ml |
| Compound 28 | 80.5% | 100 μg/ml |

Cosmetic or dermatological preparations having a content of thiazole derivatives and use thereof for treatment and/or prophylaxis of unwanted skin pigmentation are likewise advantageous embodiments of the present invention.

It is advantageous in particular, when such preparations contain 0.00001 to 10% by weight, in particular 0.001 to 3% by weight, very particularly 0.005 to 1% by weight, of one or more of the thiazole derivatives used according to the invention, based on the total weight of the preparation.

Cosmetic and dermatological preparations according to the invention can be present in various forms. Thus, they can be, e.g., a solution, an anhydrous preparation, an emulsion or microemulsion of the water-in-oil (W/O) type, or of the oil-in-water (O/W) type, a multiple emulsion, for example of the water-in-oil-in-water (W/O/W) type, a gel, a solid stick, an ointment or else an aerosol. It is also advantageous according to the invention to administer the substances used according to the invention and/or derivatives thereof in encapsulated form, e.g. in collagen matrices and other usual encapsulation materials, e.g. as cellulose encapsulations, encapsulated in gelatin or liposomally.

It is also possible and advantageous in the context of the present invention to add the substances used according to the invention and/or derivatives thereof to aqueous systems or surfactant preparations for cleaning the skin and hair.

The cosmetic and dermatological preparations according to the invention can contain cosmetic auxiliaries, as are usually used in such preparations, e.g. preservatives, bacteriocides, perfumes, substances for preventing foaming, dyes, pigments which have a coloring action, thickeners, surface-active substances, emulsifiers, softening, moistening and/or moisture-retaining substances, fats, oils, waxes or other usual constituents of a cosmetic or dermatological formulation such as alcohols, polyols, polymers, foam stabilizers, electrolytes, organic solvents or silicone derivatives.

The lipid phase can advantageously be selected from the following substance group:

mineral oils, mineral waxes
  oils, such as triglycerides of capric acid or caprylic acid, in addition natural oils such as, e.g., castor oil;
  fats, waxes and other natural and synthetic fat bodies, preferably esters of fatty acids with alcohols of low carbon number, e.g. with isopropanol, propylene glycol or glycerol, or esters of fatty alcohol with alkanoic acids of low carbon number or with fatty acids;
  alkyl benzoates;
  silicone oils such as dimethylpolysiloxanes, diethylpolysiloxanes, diphenylpolysiloxanes and mixed forms thereof.

The oil phase of the emulsions, oleogels or hydrodispersions or lipodispersions in the context of the present invention is advantageously selected from the group of esters of saturated and/or unsaturated, branched and/or unbranched alkanecarboxylic acids of a chain length of 3 to 30 C atoms and saturated and/or unsaturated, branched and/or unbranched alcohols of a chain length of 3 to 30 C atoms, from the group of esters of aromatic carboxylic acids and saturated and/or unsaturated, branched and/or unbranched alcohols of a chain length of 3 to 30 C atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate as well as synthetic, semisynthetic and natural mixtures of such esters, e.g. jojoba oil.

The aqueous phase of the preparations according to the invention optionally advantageously contains moisture-retention agents such as, e.g., propylene glycol or panthenol, and also, in particular, one or more thickeners, which can advantageously be selected from the group silicon dioxide, aluminum silicates, hydroxypropylmethylcellulose, particularly advantageously a polyacrylate such as, for example, Carbopole type 980, in each case individually or in combination.

In particular, mixtures of the abovementioned solvents can be used. In the case of alcoholic solvents, water can be a further constituent.

Emulsions according to the invention are advantageous and contain, e.g., said fats, oils, waxes and other fat bodies, and also water and an emulsifier, as is usually used for such a type of formulation.

Gels according to the invention usually contain alcohols of a low carbon number, e.g. ethanol, propylene glycol and water or an abovementioned oil in the presence of a thickener that, in the case of oily-alcoholic gels, is preferably silicon dioxide or an aluminum silicate, in the case of aqueous-alcoholic or alcoholic gels, is preferably a polyacrylate.

As propellants for preparations according to the invention that are sprayable from aerosol containers, the usual known readily volatile liquefied propellants, for example hydrocarbons (propane, butane, isobutane) are suitable, and can be used alone or in a mixture with one another. Compressed air may also be used advantageously.

Advantageously, preparations according to the invention can in addition contain substances that absorb UV radiation in the UVB range, wherein the total amount of the filter substances is, e.g., 0.1 by weight to 30% by weight, preferably 0.5 to 10% by weight, in particular 1.0 to 6.0% by weight, based on the total weight of the preparations, in order to provide cosmetic preparations which protect the hair or the skin from the entire range of ultraviolet radiation. They can also have sun protection agents for hair or skin.

The examples hereinafter are intended to illustrate the present invention without restricting it. All quantities, fractions and percentage fractions are, unless otherwise stated, percentages by weight, based on the weight and the total amount or on the total weight of the preparations.

O/W Emulsion

|  | Fraction (%) |
| --- | --- |
| Cetearyl glucoside | 1.5 |
| Ceteraryl alcohol | 5.0 |
| Caprylic/capric triglyceride | 3.0 |
| Dicaprylyl carbonate | 4.0 |
| C12-15 Alkyl benzoate | 3.0 |

-continued

| | Fraction (%) |
|---|---|
| Cyclomethicone | 2.0 |
| Propylene glycol | 5.0 |
| Panthenol | 1.0 |
| Sodium hydroxide | q.s. |
| 4-(2-Pyrimidin-2-ylamino)thiazol-4-yl)benzene-1,3-diol | 0.1 |
| Water | to 100 | pH: 5-6

What is claimed is:

1. A cosmetic or dermatological preparation, wherein the preparation comprises one or more thiazoles of formula:

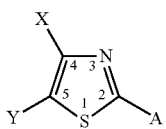

in which
A=—NH($R_1$), $R_1$ being selected from —C=O-alkyl (linear and branched), —C=O-alkenyl (linear and branched), —C=O—$C_1$-$C_8$-cycloalkyl, —C=O-aryl, —C=O-heteroaryl, —C=O-alkylaryl (linear and branched), and —C=O-alkylheteroaryl (linear and branched);
X=$C_1$-$C_8$-cycloalkyl, $C_1$-$C_{24}$-alkylaryl (linear and branched), $C_1$-$C_{24}$-alkylheteroaryl (linear and branched), 4-hydroxyphenyl, 4-methoxyphenyl, 2,4-dihydroxyphenyl, 2,3-dihydroxyphenyl, 2,4-dimethoxyphenyl, or 2,3-dimethoxyphenyl;
Y=H, $C_1$-$C_{24}$-alkyl (linear and branched), $C_1$-$C_{24}$-alkenyl (linear and branched), $C_1$-$C_8$-cycloalkyl, $C_1$-$C_{24}$-aryl, $C_1$-$C_{24}$-heteroaryl, $C_1$-$C_{24}$-alkylaryl (linear and branched), $C_1$-$C_{24}$-alkylheteroaryl (linear and branched), aryl, phenyl, 2,4-dihydroxyphenyl, 2,3-dihydroxyphenyl, 2,4-dimethoxyphenyl, 2,3-dimethoxyphenyl, —COO-alkyl, —COO-alkenyl, —COO-cycloalkyl, —COO-aryl, —COO-heteroaryl;
and X and Y together may form an aromatic homo- or heterocyclic ring system having up to n ring-forming atoms, wherein n can have values from 5 to 8, and the respective ring system in turn may be substituted by up to n–1 substituents selected from one or more of alkyl groups, hydroxyl groups, carboxyl groups, amino groups, nitrile groups, sulfur-containing substituents, ester groups, and ether groups;
and/or a thiazole of formula:

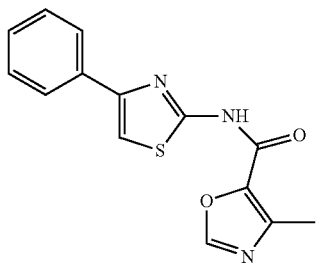 [SMILES: Cc1ncoc1C(=O)Nc1nc(-c2ccccc2)cs1]

the one or more thiazoles being present as free base or as cosmetically and dermatologically acceptable salt thereof.

2. The preparation of claim 1, wherein Y represents H.

3. The preparation of claim 1, wherein $R_1$ represents —C=O-alkyl (linear and branched).

4. The preparation of claim 2, wherein $R_1$ represents —C=O-alkyl (linear and branched).

5. The preparation of claim 1, wherein the one or more thiazoles comprise at least one compound of formula:

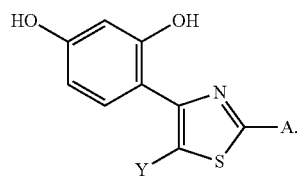

6. The preparation of claim 5, wherein Y represents H.

7. The preparation of claim 5, wherein $R_1$ represents —C=O-alkyl (linear and branched).

8. The preparation of claim 6, wherein $R_1$ represents —C=O-alkyl (linear and branched).

9. The preparation of claim 1, wherein the one or more thiazoles comprise at least one of the following compounds:

Compound 8

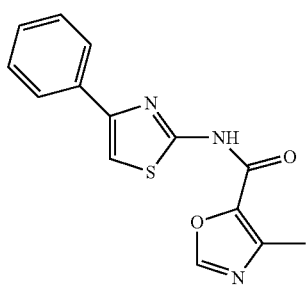

Compound 9

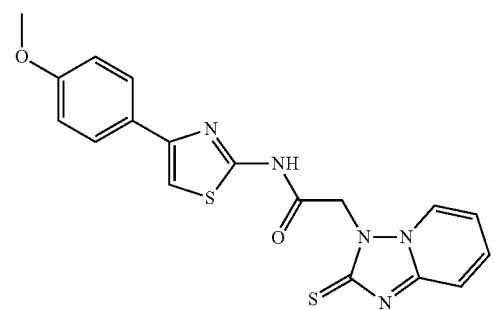

Compound 11

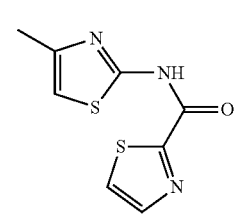

-continued

Compound 15

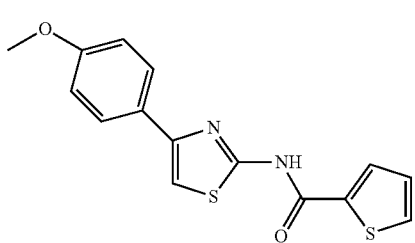

Compound 26

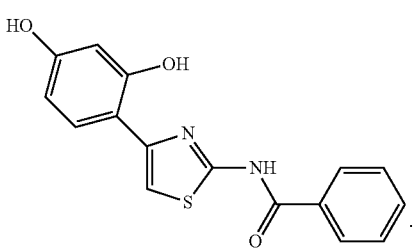

10. The preparation of claim 1, wherein at least one of the one or more thiazoles is present as a halide, a carbonate, an ascorbate, an acetate, or a phosphate.

11. The preparation of claim 1, wherein the one or more thiazoles are present in a total concentration of from 0.00001% to 10% by weight.

12. The preparation of claim 1, wherein the one or more thiazoles are present in a total concentration of from 0.001% to 3.0% by weight.

13. The preparation of claim 1, wherein the one or more thiazoles are present in a total concentration of from 0.005% to 1.0% by weight.

14. The preparation of claim 1, wherein X represents 4-methoxyphenyl.

15. The preparation of claim 1, wherein $R_1$ is selected from —C=O-heteroaryl.

16. A cosmetic or dermatological preparation, wherein the preparation comprises one or more thiazoles of formula:

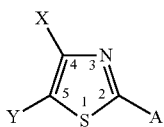

in which

A=—N($R_1$)$_2$, —S—$R_1$, —C—($R_1$)$_3$, —O—$R_1$, —CO—$R_1$, -morpholino, -morpholino derivatives;

$R_1$, X and Y can be different, in part identical or completely identical and, independently of one another represent:

$R_1$=H, $C_1$-$C_{24}$-alkyl (linear and branched), $C_1$-$C_{24}$-alkenyl (linear and branched), $C_1$-$C_{24}$-hydroxyalkyl (linear and branched), $C_1$-$C_8$-cycloalkyl, $C_1$-$C_{24}$-aryl, $C_1$-$C_{24}$-heteroaryl, $C_1$-$C_{24}$-alkylheteroaryl (linear and branched), 2-hydroxyphenyl, 3-hydroxyphenyl, 4-hydroxyphenyl, 4-cyanophenyl, pyridin-2-yl, pyridin-3-yl, pyridin-4-yl, pyridin-1(2H)-yl, pyrimidin-2-yl, pyrazin-2-yl, pyrimidin-4-yl, pyridazin-3-yl, pyridazin-4-yl, pyrimidin-2-yl, pyrimidin-5-yl, 1,2,4-triazin-3-yl, 1,3,5-triazin-2-yl, 1,2,3-triazin-4-yl, 1,2,3-triazin-5-yl, 1,2,3,4-tetrazin-5-yl, 1,2,3,5-tetrazin-4-yl, 1,2,4,5-tetrazin-3-yl, pentazin-6-yl, morpholino, thiazole, —C=O-alkyl (linear and branched), —C=O-alkenyl (linear and branched), —C=O—$C_1$-$C_8$-cycloalkyl, —C=O-aryl, —C=O-heteroaryl, —C=O-alkylaryl (linear and branched), —C=O— alkylheteroaryl (linear and branched), —C=O—NH-alkyl (linear and branched), —C=O—NH-alkenyl (linear and branched), —C=O—NH-cycloalkyl, —C=O—NH-aryl, —C=O—NH-heteroaryl, —C=O—NH-alkylaryl (linear and branched), —C=O—NH-alkylheteroaryl (linear and branched);

X=$C_1$-$C_8$-cycloalkyl, $C_1$-$C_{24}$-alkylaryl (linear and branched), $C_1$-$C_{24}$-alkylheteroaryl (linear and branched), 4-hydroxyphenyl, 4-methoxyphenyl, 2,4-dihydroxyphenyl, 2,3-dihydroxyphenyl, 2,4-dimethoxyphenyl, 2,3-dimethoxyphenyl;

Y=H, $C_1$-$C_{24}$-alkyl (linear and branched), $C_1$-$C_{24}$-alkenyl (linear and branched), $C_1$-$C_8$-cycloalkyl, $C_1$-$C_{24}$-aryl, $C_1$-$C_{24}$-heteroaryl, $C_1$-$C_{24}$-alkylaryl (linear and branched), $C_1$-$C_{24}$-alkylheteroaryl (linear and branched), aryl, phenyl, 2,4-dihydroxyphenyl, 2,3-dihydroxyphenyl, 2,4-dimethoxyphenyl, 2,3-dimethoxyphenyl, —COO-alkyl, —COO-alkenyl, —COO-cycloalkyl, —COO-aryl, —COO-heteroaryl;

and in which X and Y together may form an aromatic homo- or heterocyclic ring system having up to n ring-forming atoms, wherein n can have values from 5 to 8, and the respective ring system in turn may be substituted by up to n−1 substituents selected from one or more of alkyl groups, hydroxyl groups, carboxyl groups, amino groups, nitrile groups, sulfur-containing substituents, ester groups, and ether groups;

and/or one or more thiazoles of the following formulae:

Compound 10

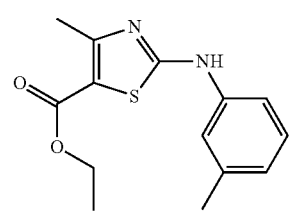

Compound 14

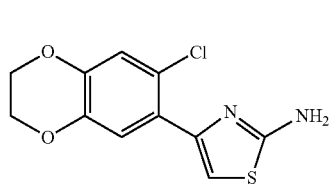

Compound 28

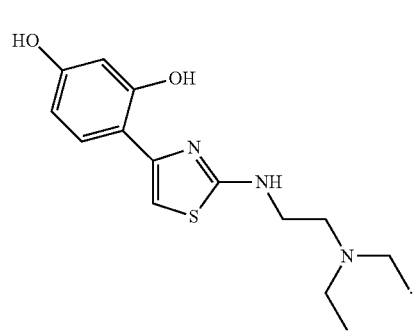

-continued

Compound 4

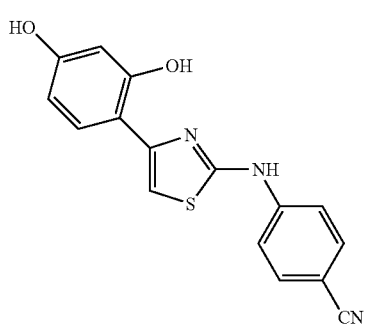

the one or more thiazoles being present as free base or as cosmetically and dermatologically acceptable salt thereof, provided that at least one of the one or more thiazoles is present as a halide, a carbonate, an ascorbate, an acetate, or a phosphate.

17. The preparation of claim 16, wherein Y represents H.

18. The preparation of claim 16, wherein X represents 4-methoxyphenyl or 2,4-dihydroxyphenyl.

19. A method of treating undesirable skin pigmentation, wherein the method comprises applying to skin of a patient in need thereof the preparation of claim 1 in an amount which is sufficient for treating undesirable skin pigmentation.

20. A method of treating undesirable skin pigmentation, wherein the method comprises applying to skin of a patient in need thereof the preparation of claim 16 in an amount which is sufficient for treating undesirable skin pigmentation.

* * * * *